(12) United States Patent
Yao et al.

(10) Patent No.: US 9,339,585 B2
(45) Date of Patent: May 17, 2016

(54) POROUS COATING FOR SURGICAL ORTHOPEDIC IMPLANTS

(71) Applicant: Kennametal Inc., Latrobe, PA (US)

(72) Inventors: Matthew Yao, Belleville (CA); Rachel Collier, Belleville (CA); Abdelhakim Belhadjhamida, Belleville (CA); Danie DeWet, Kingston (CA)

(73) Assignee: KENNAMETAL INC., Latrobe, PA (US)

( * ) Notice: Subject to any disclaimer, the term of this patent is extended or adjusted under 35 U.S.C. 154(b) by 0 days.

(21) Appl. No.: 14/244,633

(22) Filed: Apr. 3, 2014

(65) Prior Publication Data

US 2015/0283295 A1 Oct. 8, 2015

(51) Int. Cl.
 *B22F 7/04* (2006.01)
 *A61L 27/04* (2006.01)
 *A61L 27/30* (2006.01)

(52) U.S. Cl.
 CPC .............. *A61L 27/045* (2013.01); *A61L 27/306* (2013.01); *A61L 2420/02* (2013.01); *A61L 2430/02* (2013.01); *Y10T 428/12042* (2015.01)

(58) Field of Classification Search
 None
 See application file for complete search history.

(56) References Cited

U.S. PATENT DOCUMENTS

| | | | |
|---|---|---|---|
| 3,855,638 A | 12/1974 | Pilliar | |
| 4,156,943 A | 6/1979 | Collier | |
| 4,644,942 A | 2/1987 | Sump | |
| 5,004,476 A * | 4/1991 | Cook | 623/23.3 |
| 5,104,410 A | 4/1992 | Chowdhary | |
| 5,263,986 A | 11/1993 | Noiles et al. | |
| 5,358,533 A | 10/1994 | Noiles et al. | |
| 5,443,510 A | 8/1995 | Shetty et al. | |
| 6,132,674 A * | 10/2000 | Compton et al. | 419/2 |
| 6,945,448 B2 | 9/2005 | Medlin et al. | |
| 7,241,313 B2 | 7/2007 | Unwin et al. | |
| 7,520,947 B2 * | 4/2009 | Kennedy et al. | 148/674 |
| 8,066,770 B2 * | 11/2011 | Rivard et al. | 623/16.11 |
| 8,124,187 B2 | 2/2012 | Su et al. | |
| 2010/0209666 A1 | 8/2010 | Rivard et al. | |

OTHER PUBLICATIONS

Webster et al., "Increased osteoblast adhesion on nanophase metals: Ti, Ti6Al4V, and CoCrMo", 2004, Biomaterials, vol. 25, pp. 4731-4739.*
Welsh et al., "Surgical implants: the role of surface porosity in fixation to bone and acrylic", J Bone Joint Surg Am. Jul. 1971;53(5):963-77.
Pilliar et al., "Porous surface layered prosthetic devices", Biomedical Engineering, Apr. 1975;10(4):126-31.

(Continued)

*Primary Examiner* — Humera Sheikh
*Assistant Examiner* — Seth Dumbris
(74) *Attorney, Agent, or Firm* — Larry R. Meenan

(57) ABSTRACT

A surgical implant component comprising an implant component body manufactured from a Co-based substrate alloy comprising Co, Cr, Mo, Si, and C, and a coating on a bone-ingrowth surface of the component body manufactured from a Co-based coating alloy comprising Co, Cr, Mo, Si, C and B. The coating is a network of fused particles of the Co-based coating alloy with spherical particles, irregular aspherical particles, and between about 35 and about 70 volume % porosity. A method of manufacturing the foregoing surgical implant component.

13 Claims, 7 Drawing Sheets

(56) References Cited

OTHER PUBLICATIONS

Bobyn et al., "The optimum pore size for the fixation of porous-surfaced metal implants by the ingrowth of bone", Clin Orthop Relat Res. Jul.-Aug. 1980;(150):263-70.

Mishra et al., Metallurgy, Microstructure, Chemistry and Mechanical Properties of a New Grade of Cobalt-Chromium Alloy Before and After Porous-Coating; Proceedings of ASM Symposium on Cobalt-Base Alloys for Biomedical Applications; 1999, pp. 71-88.

* cited by examiner

POROUS COATING FOR SURGICAL ORTHOPEDIC IMPLANTS

FIELD OF THE INVENTION

This invention is directed to surgical orthopedic implants and a porous coating which enhances bone in-growth characteristics for surgical orthopedic implants.

BACKGROUND OF THE INVENTION

A cobalt-chromium-molybdenum (Co—Cr—Mo) metallic alloy specified by ASTM F75 is commonly used for surgical implants such as for prosthetic knees, hips, shoulders, elbows, wrists, ankles, fingers, toes and spinal elements because of the alloy's strength, corrosion resistance, and biocompatibility. This Co—Cr—Mo alloy has greater wear resistance than stainless steels and titanium alloys. The nominal composition of the F75 alloy is 27.00 to 30.00% Cr, 5.00 to 7.00% Mo, 0.35% C maximum, 1.0% Si maximum, 1.0% Mn maximum, 0.50% Ni maximum, 0.75% Fe maximum, 0.010% B maximum, with balance of Co and other inevitable trace elements and impurities. All percentages herein are by weight, unless indicated otherwise.

Welsh et al., Surgical implants: the role of surface porosity in fixation to bone and acrylic. J Bone and Joint Surg Am 53: 963, 1971 and Pilliar et al., Porous surface layered prosthetic devices. Biomed Eng 10:126, 1975, described implants having a porous Co-based alloy coating of gas-atomized spheres on a substrate of the same composition to provide open surface porosity for bony ingrowth. Bobyn et al., The optimum pore size for the fixation of porous-surfaced metal implants by the ingrowth of bone. Clin Orthop 150: 263, 1980, study the impact of distinct surface-coating pore size on fixation of implants.

Rivard et al. U.S. Pat. No. 8,383,187 describe manufacturing a surgical implant by applying aspherical metallic particles to a substrate.

There is need for commercially available coating systems for surgical implants which cost-effectively address the needs for such coatings in terms of porosity, strength, wear-resistance, friction, and manufacturability.

SUMMARY OF THE INVENTION

Briefly, therefore, the invention is directed to a surgical implant component comprising an implant component body manufactured from a Co-based substrate alloy comprising Co, Cr, Mo, Si, and C; and a coating on a bone-ingrowth surface of the component body manufactured from a Co-based coating alloy comprising Co, Cr, Mo, Si, C and B; wherein the coating is a network of fused particles of the Co-based coating alloy with the particles including between 60 and 90 volume % spherical particles and between 10 and 40 volume % irregular aspherical particles; wherein the coating further comprises pores and between about 35 and about 70 volume % porosity.

In another aspect, the invention is directed to a method of manufacturing a surgical implant comprising applying a metal slurry comprising solvent, binder, and metal particles of a Co-based coating alloy comprising Co, Cr, Mo, Si, C and B to a bone ingrowth surface of a surgical implant substrate of a Co-based substrate alloy comprising Co, Cr, Mo, Si, and C; and heating to remove the solvent and binder and to sinter the Co-based coating alloy to form a porous Co-based alloy coating on the surface of the metallic component; wherein the metal particles include between about 60 and about 90 volume % spherical particles and between about 10 and about 40 volume % irregular aspherical particles.

Other objects and features of the invention will be in part apparent and in part pointed out hereinafter.

DETAILED DESCRIPTION OF PREFERRED EMBODIMENTS

The present invention is a Co—Cr—Mo component of an orthopedic implant, a coating on an orthopedic implant, a coating material for an orthopedic implant, and a coating method for an orthopedic implant. The orthopedic implant is for any one of knees, hips, shoulders, elbows, wrists, ankles, fingers, toes or spinal elements.

Figure 1:
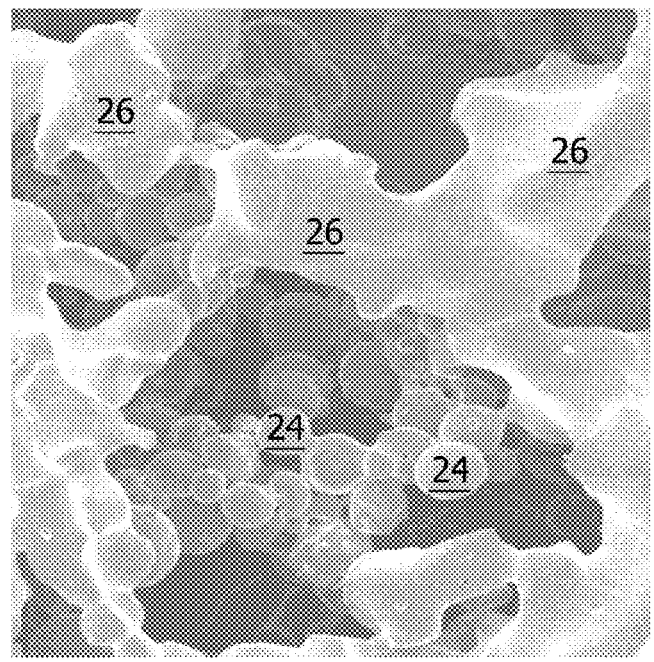
FIG. 1 is a photomicrograph at 130× of a coating of the invention.

The invention is based on a discovery that a coating on a surgical implant substrate has improved bone ingrowth performance if the coating comprises a particular mixture of fused particles which impart desired porosity and surface roughness. The particular mixture of fused particles in the coating of the invention includes relatively smaller spherical particles and relatively larger irregular aspherical particles as illustrated in FIG. 1. The preferred coating is a network of fused particles of the Co-based coating alloy with the particles including between 60 and 90 volume % spherical particles and between 10 and 40 volume % irregular aspherical particles. In one preferred embodiment, the coating is a network of the fused particles with the particles including between 65 and 75 volume % spherical particles and between 25 and 35 volume % irregular aspherical particles. The coating is preferably applied by slurry deposition and sintering of the coating to a surgical implant component substrate comprising a Co-based substrate alloy. The particle components of the Co-based coating alloy fuse to the substrate during sintering and also fuse to each other, as shown in FIG. 1, which is a photomicrograph of the coating at 130×. The preferred mechanism of forming the rough porous coating is liquid phase sintering.

In one embodiment of the invention, the spherical particles have a particle size such that at least about 75 vol %, preferably at least about 90 vol %, of the spherical particles have a particle size between about 75 and about 150 microns. The irregular aspherical particles have a particle size such that at least about 75 vol %, preferably at least about 90 vol % of the irregular aspherical particles have a particle size between about 355 and about 425 microns. The relative fine spherical Co—Cr—Mo powders facilitate sintering and the relative larger irregular shaped Co—Cr—Mo powders enhance the surface roughness of the porous coating. Particle size refers to the largest cross-sectional dimension of the particle. For spherical particles, this refers to the diameter. Accordingly, the invention in this preferred embodiment employs as a coating material a mixture of relatively small spherical particles in combination with relatively larger aspherical particles.

Figure 2:
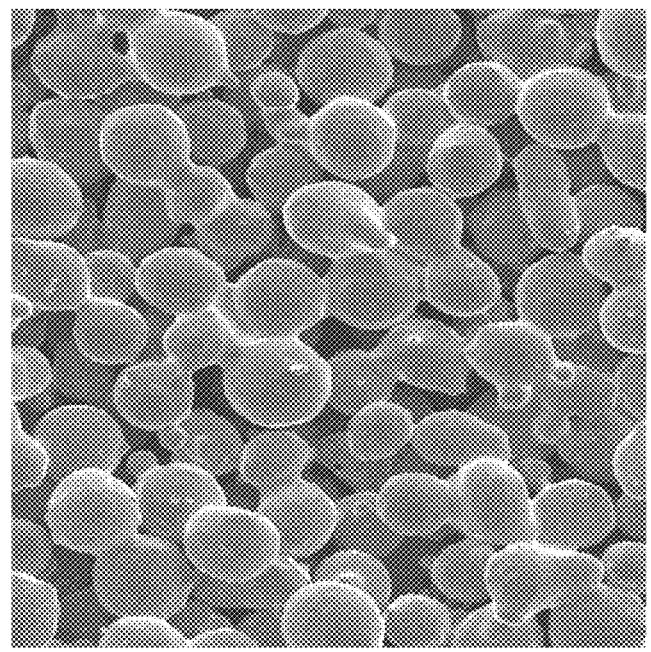
FIGS. 2 and 3 are photomicrographs at 100× and 35×, respectively, of coatings not of the invention, for comparison purposes.

The spherical particles are spherical in the sense that they are generally and substantially spherical, but not perfectly spherical. FIG. 2 is a photomicrograph at 100× showing a collection of sintered spherical particles of the type employed in the invention. Some natural distortion to slightly elliptical shape inevitably occurs during forming the particles and sintering. It will therefore be understood that spherical particles in accordance with this invention are generally spherical in that the diameter is relatively consistent in all cross sections. The spherical particles employed in the invention are preferably prepared by a standard gas atomization process. Accordingly, the particles are more spherical before sintering than after sintering. But after sintering and forming of the coating, they do not lose their generally spherical character as shown in FIG. 2, and as depicted by the spherical particles in FIG. 1.

Figure 3:
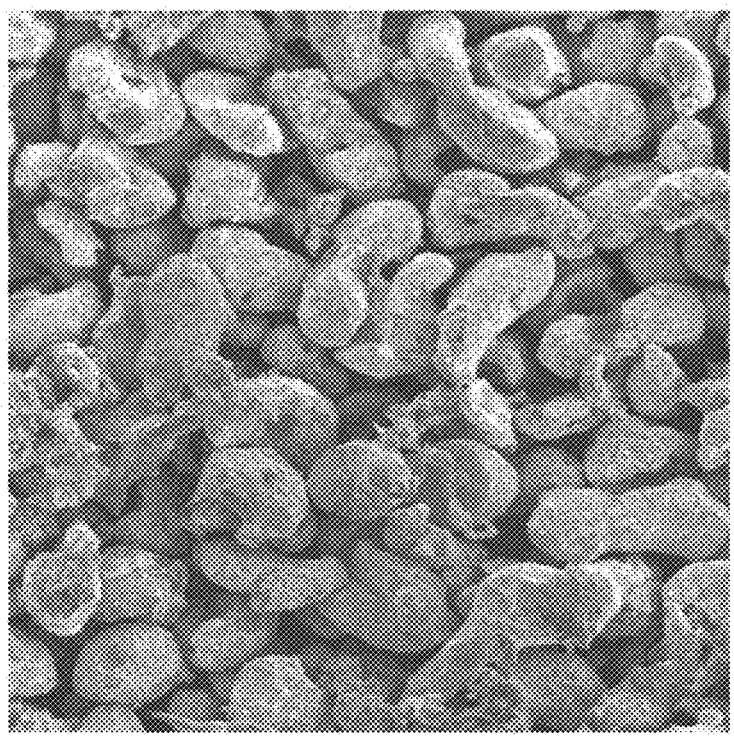

For irregular aspherical particles, the particle size dimension is also the largest cross-sectional dimension, as it can be seen that such particles typically have a length dimension in one direction that is longer than a corresponding width dimension. FIG. 3 is a photomicrograph at 35× showing a collection of sintered aspherical particles of the type employed in the invention. The irregular aspherical particles employed in the invention are prepared by a standard water atomization process.

The sintered arrays shown in FIGS. 2 and 3 are not coatings of the invention, as coatings of the invention contain significant quantities of both spherical and aspherical particles, as shown in FIG. 1. But the sintered arrays in FIGS. 2 and 3 are instructive as to the significant advantage applicants have discovered of their carefully tailored particle mixture. In particular, the spherical particles in FIG. 2 were able to sinter together well at a reasonably low sintering temperature of 2380° F. (1305° C.), but the resulting porosity is less than desired (<35%), and there is insufficient surface roughness. The irregular aspherical particles in FIG. 3, in contrast, did not sinter well even at 2380° F. (1305° C.). To obtain a sufficient degree of sintering to meet strength requirements would require higher temperatures, which would in turn risk negatively impacting the properties of the Co—Cr—Mo substrate, and increase energy input requirements.

The coating of the invention has a porosity of at least 35 vol %, and in certain embodiments, preferably at least 50 vol %. The porosity is maintained below 70 vol %, as too high of a porosity corresponds to weakness, and weakly bonded particles can become dislodged from the coating act as a third body interfering with two articulating parts, accelerating wear. Porosity in the inventive coating is therefore between 35 and 70 vol %, for example between about 50 and about 70 vol %. Porosity is measured using Clemex Image Analysis Software—Vision Lite 7.0, and reference to ASTM F 1854—*Standard Test Method for Stereological Evaluation of Porous Coatings on Medical Implants*. A maximum field of view measuring 2383.61 µm×1787.71 µm at ×50 magnification is available with this microscope and software. Ten fields of view were chosen to evaluate the sample. Commercially available Trabecular Metal™ porous coating with known porosity is used as calibration.

The pore size is also important, as bone tissue cannot grow into pores that are too small, and grows only very slowly into pores that are too large. Having a substantial portion of the pores having a pore size between 100 and 250 microns provides excellent bone in-growth properties. In the preferred embodiment, at least about 75 vol % of the pore volume in the coating is manifest by pores between about 100 and 250 microns in size. Pore size is measured using Trabecular Metal™ as a baseline, with the pore size determined by line intercept analysis using the same Clemex Image Analysis Software—Vision Lite 7.0, and reference to ASTM F 1854—*Standard Test Method for Stereological Evaluation of Porous Coatings on Medical Implants*. The pore size is in a range with a maximum and minimum, and the average size is reported as the pore size. The invention therefore employs space-holder particles in the coating alloy particle slurry to impart the desired porosity volume and pore size. It has been discovered that space-holder particles, for example space-holder beads, of various sizes ranging from 75 to 180 microns imparts the desired pore size. In one preferred embodiment, the space-holder particles are sized such that at least about 90 vol % of the particles are within the range of 75 to 180 microns. The space-holder size and pore size do not precisely correspond. For example a 75-180 micron space holder size has been found to impart 100-250 micron pore size. The space-holder particles are manufactured from a material which is, for example, an acrylic homopolymer. The material selected for the space-holder particle must volatilize at low temperature, for example, less than about 950° F. (510° C.). In one embodiment, for example, the space-holder particles have a volatilization temperature of about 570° F. (300° C.), and upon heating to sintering temperature, the composite is held at about 900° F. (480° C.) for about 30 minutes to permit volatilization of the space-holder particles. The space-holder particles are non-metallic. It can be seen in FIG. 5 that the space-holder particles also facilitate imparting the desired surface roughness. In the currently preferred embodiment, the space-holder particles are space-holder beads.

Figure 4:
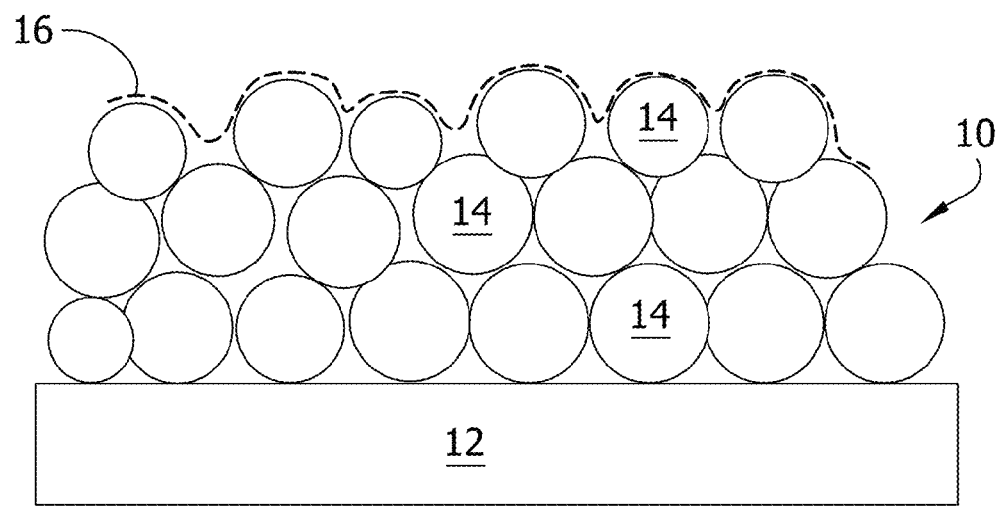
FIG. 4 is a schematic representation of a coating not of the invention, for comparison purposes.
Figure 5:
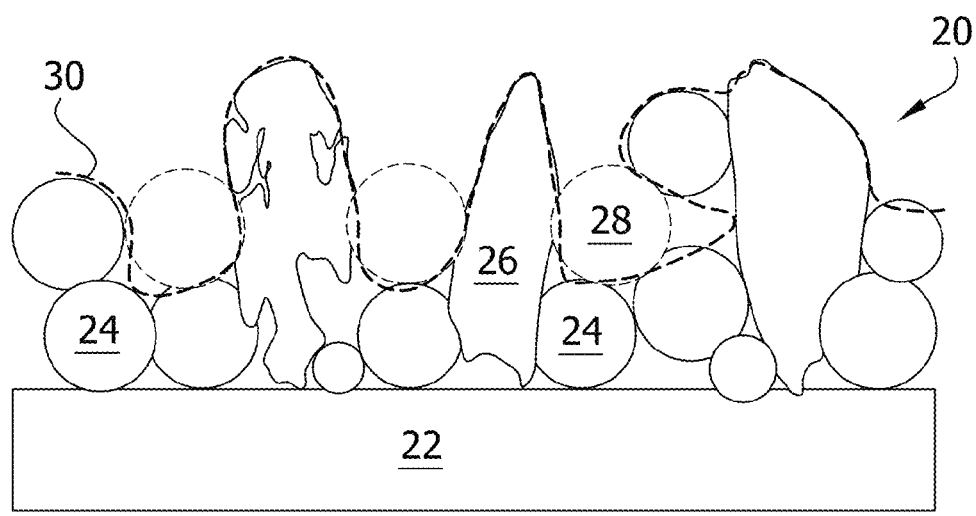
FIG. 5 is a schematic representation of a coating of the invention.

The mixture of spherical particles and irregular aspherical particles therefore serves one function of allowing for adjustment and control of the pore size and porosity. The particle mixture aspect also facilitates the sintering to enhance intra-particle bonding and bonding of the coating particles to the implant substrate. Furthermore, the mixture aspect also allows for increase in surface roughness of the porous coating and concomitant increase in the friction between coating and the contact bone. FIGS. 4 and 5 schematically demonstrate the enhanced roughness achieved in FIG. 5 with irregular aspherical particles in combination with spherical particles, as aided by the volatilized space-holder particles, in comparison to the surface roughness of coating of FIG. 4. FIG. 4 shows coating 10 on substrate 12 with powder particles 14 to form a surface having roughness 16. In contrast, it can be seen in FIG. 5 that coating 20 has a rougher surface 30 formed by the combination of spherical particles 24, aspherical particles 26, and space-holder beads 28. See FIG. 1 for the nature of the spherical and aspherical particles 26 and 28 in the final coating after sintering. Upon volatilization of the space-holder beads 28, it can be seen that a much rougher surface results, having the contour shown at 30. FIGS. 4 and 5 are in a schematic format which emphasizes the nature of the particles. In an actual sintered coating, the spherical particles shown in FIG. 4 are more fused together and the spherical shapes are distorted. Similarly, in FIG. 5, after sintering, the spherical and aspherical particles are more fused together and their shapes are distorted versus the shapes shown here, and the space-holder particles at 28 are not present, having been volatilized.

The enhanced surface roughness of the invention manifests a coefficient of friction of at least about 0.55, preferably at least about 0.65. This is in contrast to a coefficient of friction of 0.53 in prior art F-75 coatings. The greater coefficient of friction is critical to improving bone ingrowth, as the greater friction decreases micro-scale motion of the implanted device. Micro-scale motion is a leading inhibitor of bone ingrowth, as even the slightest movement of the implant relative to the bone disrupts growth. The rough porous coating of the invention as illustrated in FIG. 1 provides initial implant stability as the enhanced roughness and increased coefficient of friction minimizes micro-scale movement of the implant as it grips against bone more solidly. Short- and long-term in-growth are also enhanced through the random and interconnected network of pores, characterized by the porosity and pore size described herein.

The surgical implant of the invention comprises the substrate and the coating thereon, with the coating having a thickness of at least about 0.5 mm. In one embodiment, the coating has a thickness between about 0.5 and 2.5 mm.

Aside and apart from the morphology of the coating, a second aspect of this invention is the composition of the coating in comparison to the composition of the substrate. The chemical composition of Co—Cr—Mo substrate alloy and the Co—Cr—Mo coating alloy comply with ASTM F 75: Standard Specification for Cobalt-28 Chromium-6 Molybdenum Alloy Castings and Casting Alloy for Surgical Implants (UNS R30075). While both alloys employed in the invention comply with this specification, the Co-based coating alloy has a composition which is different from the composition of the Co-based substrate alloy. In particular, the Co-based coating alloy composition has an incipient melting point which is lower than the incipient melting point of the Co-based substrate alloy composition. In certain embodiments, the solidus of the coating material is at least about 10° F. (about 5° C.) lower than the solidus of the substrate, for example at least about 20° F. (about 10° C.) lower. A lower solidus temperature and the B and C content assist in sintering. This solidus temperature refers to the overall solidus temperature of the coating material, as the aspherical and spherical components may have solidi different from each other.

The purpose of the disparate melting points so that a sintering temperature may be employed which facilitates formation of a strong coating with the selected pore size and porosity. The goal is to use a sintering temperature which will produce a strong enough bond among the coating particles as well as between the coating particles and the substrate. The goal is also to avoid too high a sintering temperature which will close pores, reduce porosity, and lead to excessive grain growth in the Co—Cr—Mo substrate thereby adversely affecting its properties. The inventors have therefore discovered that the best properties of the surgical implant can be achieved if sintering temperature is minimized, at least to the extent a strong enough bond is achieved. With the understanding that slight increases in C and/or B have a significant impact on lowering both the liquidus temperature (i.e. the melting point, the temperature at which the alloy turns completely into a liquid), as well as the solidus temperature (i.e. the incipient melting temperature; i.e., the temperature at which the first drops of liquid begin to appear) in most Co—Cr—Mo alloys, the inventors formulate their coating to have a relatively higher level of C and/or B than the substrate alloy. In a preferred embodiment, the method is carried out by sintering at a temperature between about 2300 and about 2500° F. (about 1260 to about 1370° C.), such as between about 2300 and about 2430° F. (about 1260 to about 1330° C.), for example between about 2350 and about 2400° F. (about 1285 and about 1315° C.).

Stated another way, it is important in the context of this invention that both the coating composition and the substrate composition comply with ASTM F-75. If the coating composition and the substrate composition are the same, however, then exposure to the sintering temperature will affect both the substrate and the coating alloys generally the same. This is not desirable, however, because the degree of heating needed to fully sinter the coating is a degree of heating which risks adverse effects on the substrate properties. The invention addresses this by slightly modifying the composition of the substrate and the coating alloys relative to each other so that the selected sintering temperature does not have the same impact on the substrate that is has on the coating material.

The C concentration in the substrate alloy is kept at a middle level at about 0.175 wt %, which is sufficient to sustain the presence of carbides and interstitial carbon which facilitates grain boundary pinning, and consequent reduction in grain growth during the sintering process and during the heat-up and cool-down steps before and after sintering.

In one embodiment, the Co-based coating alloy contains more of one of C and/or B in the coating alloy than in the substrate alloy. For example, the Co-based coating alloy contains at least 10% more of C and/or B than is in the Co-based substrate alloy. That is, the coating alloy contains a) at least 10% more C relative to C concentration of the Co-based substrate alloy, and/or b) at least 10% more B relative to the B concentration of the Co-based substrate alloy. This means, for example, that if the Co-based substrate alloy has 0.17 wt % C and 0.002 wt % B, then the Co-based coating alloy has a) at least 0.19 wt % C, or b) at least 0.0022 wt % B, or c) at least 0.19 wt % C and at least 0.0022 wt % B. In certain embodiments, the coating alloy contains B and the substrate alloy does not contain B.

Accordingly, the substrate alloy and coating alloy in one preferred embodiment of the invention comprise the following:
   from about 27 to about 30 wt % Cr,
   from about 5 to about 7 wt % Mo,
   up to about 1.0 wt % Si,
   no more than 0.010 wt % B
   C in a concentration of up to about 0.35 wt % C,
   incidental impurities totaling less than 4 wt % including no more than 1 wt % Mn, 0.75 wt % Fe and no more than 0.5 wt % Ni, and
   balance Co.

In another embodiment the substrate alloy and coating alloy comprise the following:
   from about 23 to about 33 wt % Cr,
   from about 8 to about 20 wt % Mo,
   up to about 1.5 wr % Si,
   no more than 0.010 wt % B
   from about 1.5 to about 3.5 wt % C
   incidental impurities totaling less than 4 wt % including no more than 1 wt % Fe and no more than 1% Ni, and
   balance Co.

As a general proposition, it is preferred that the substrate affirmatively contains at least about 0.05 wt % Si and at least about 0.05 wt % Mn, and up to 1.0 wt % of each, as these elements assist flowability and deoxidizing during substrate casting. These functions are less important for powder manufacture; so these elements may be dispensed with in the coating alloy composition.

The Co-based substrate alloy and Co-based coating alloy employed in the invention generally "comprise" the foregoing components in that its advantages are germane to the positively recited requirements of the Co, Cr, Mo, Si and C content, in combination with the other recited requirements. There are certain embodiments within this general scope wherein the Co-based substrate alloy and Co-based coating alloy "consist essentially of" the positively recited alloying elements and excludes any other components which materially affect the basic and novel properties, and in any event excludes any non-recited components in a concentration above 3 wt %. In other embodiments the alloys "consist of" these compositional requirements in that other non-recited components are strictly excluded.

In carrying out the invention, a slurry is formed which contains the spherical particles, the irregular aspherical particles, the space-holder particles, a solvent, and a binder. The binder is an organic substance such as acrylic that is capable of temporarily binding the Co alloy particles until they are sintered. One preferred binder is WB4104 available from Polymer Innovations. The solvent is a fluid (e.g., water or alcohol) capable of dissolving the organic binder and in which the alloy particles will remain in suspension. The range of these major components in one embodiment of the invention is as follows:

Spherical Co-based alloy particles: 20 to 30% (Vol)
Irregular Co-based alloy particles: 5 to 15%
Space-holder particles: 20 to 25%
Solvent: 30 to 40%
Binder: 5 to 10%

For example, in one embodiment the components are mixed together as follows:

Spherical Co-based alloy particles: 24.4% (Vol)
Irregular Co-based alloy particles: 10.5%
Space-holder particles: 22.1%
Solvent: 36.6%
Binder: 6.4%

The slurry is prepared by mixing the alloy particles, space-holder particles, binder, and solvent (e.g., by agitation in a paint mixer). The surgical implant component substrate to be coated needs to be clean and smooth. The steps taken to clean and smooth the metal substrate will vary, depending on the metallurgical processes used to produce the substrate. Generally, solvents and the like are used to remove any dirt and grease from the surfaces to be coated. The metal body is ready for being coated once the surface of the metal part is clean.

Application of the slurry to the substrate is preferably achieved by dipping the substrate in the slurry. Alternatively, the slurry can be applied to the outer surface of the substrate by any method suitable for applying paint to a workpiece. Thus the slurry can be brushed, poured, rolled, and/or sprayed onto the outer surface of the substrate. The viscosity of the slurry can be adjusted to suit the method of application by controlling the proportion of solvent in the slurry. Further, the slurry can be applied to only selected portions of the substrate using any of the foregoing methods or combinations thereof. Thus, the slurry is easily applied to the outer surface of the substrate regardless of the geometry of the metal body. Once the slurry is applied to the substrate, it is allowed to dry (e.g., air dry) until the solvent has substantially evaporated.

After the solvent has evaporated, the component is placed in a furnace to drive off the organic binder and to sinter the Co powder particles and to bond the porous coating to the Co substrate. The atmosphere in the furnace is preferably a non-oxidizing atmosphere (e.g., inert gas or a vacuum). In one example, sintering is performed at a temperature in the range of 2350 to 2400° F. (about 1285 and about 1315° C.) for about 30 minutes.

The invention will be further illustrated by the following working examples.

EXAMPLE I

A Co-based coating using a spherical and aspherical powder blend was applied to a Co-based substrate as follows:

| Material | Co | Cr | Mo | C | Si | B | Fe | Ni | Mn |
|---|---|---|---|---|---|---|---|---|---|
| Spherical Powder | Bal. | 28.89 | 6.04 | 0.26 | 0.56 | 0.008 | 0.55 | 0.08 | 0.23 |
| Aspherical Powder | Bal. | 27.88 | 5.60 | 0.22 | 0.51 | 0.007 | 0.41 | 0.31 | 0.05 |
| Substrate | Bal. | 28.43 | 5.91 | 0.17 | 0.75 | 0.002 | 0.50 | 0.15 | 0.41 |

The ratio of spherical particles to aspherical particles in the coating mixture was 7/3. The size of the spherical particles was between about 75 and about 150 microns. The size of the aspherical particles was between about 355 and about 425 microns. The slurry contained 24.4% spherical particles, 10.5% aspherical particles, 22.1% space-holder beads, 6.4% binder, and 36.6% solvent. The coating thickness was 2 mm. The sintering temperature was 2380° F. (1305° C.) for 30 minutes. A photomicrograph of the coating was taken and is presented in FIG. 1

EXAMPLE II

The static tensile strength of the coating of the invention was evaluated under ASTM F-1147. A Co-based coating was applied to a Co-based substrate according to the parameters of Example I. The coating thickness was 2 mm. The tensile strength was determined to be over 60 MPa, which substantially exceeds the 22 MPa recommended under F-1147.

EXAMPLE III

In order to investigate whether the organic binder used in the coating method of the invention leaves a C residue, two porous coating samples according to Example I were subjected to carbon analysis. The coatings were determined to have C contents of 0.25 wt % and 0.23 wt %, well within the 0.35 max C wt % of ASTM F 75.

EXAMPLE IV

Figure 6:
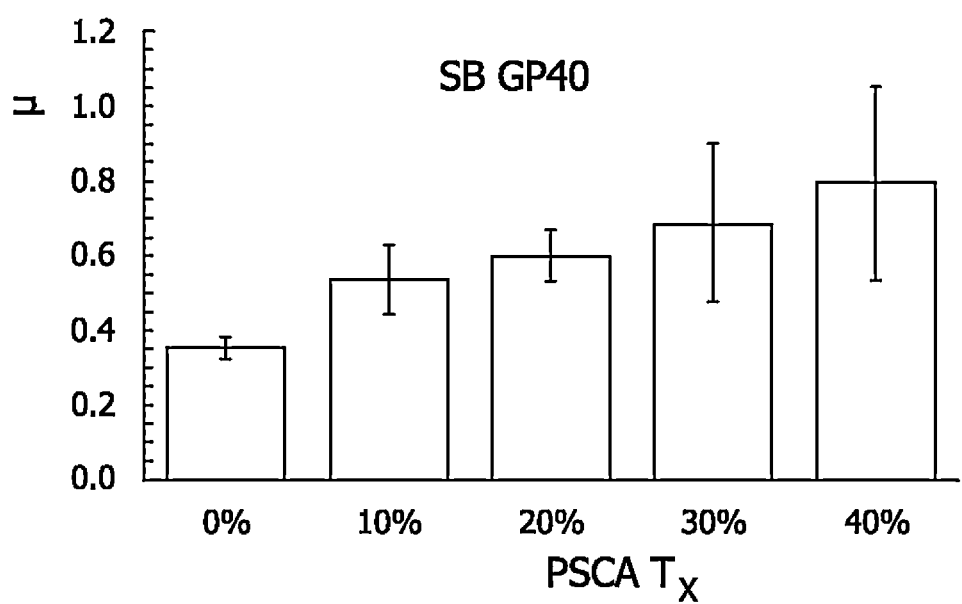
FIG. 6 is a graph of friction data collected in accordance with a working example.

Experiments were conducted to determine coefficient of friction characteristics of the coating of the invention in contact with simulated bone material. Friction forces were determined between the coating of the invention in contact with top and bottom surfaces of simulated bone material cubes. The results are shown in FIG. 6. The legend PSCA Tx represents four variations of the coating of the invention, with the 0%, 10%, 20%, 30% and 40% representing percentage of irregular aspherical powder. The average coefficient of friction µ increases from slightly under 0.4 to nearly 0.8, demonstrating that increasing the surface roughness in accordance with this invention increases the coefficient of friction of the coating in contact with the simulated bone material SB GP40.

EXAMPLE V

A Co-based coating was applied to a Co-based implant substrates as follows:

| Material | Co | Cr | Mo | C | Si | B | Fe | Ni | Mn |
|---|---|---|---|---|---|---|---|---|---|
| Spherical Powder | Bal. | 28.89 | 6.04 | 0.26 | 0.56 | 0.008 | 0.55 | 0.08 | 0.23 |
| Aspherical Powder | Bal. | 27.88 | 5.60 | 0.22 | 0.51 | 0.007 | 0.41 | 0.31 | 0.05 |
| Substrate | Bal. | 28.43 | 5.91 | 0.17 | 0.75 | 0.002 | 0.50 | 0.15 | 0.41 |

Figure 7:
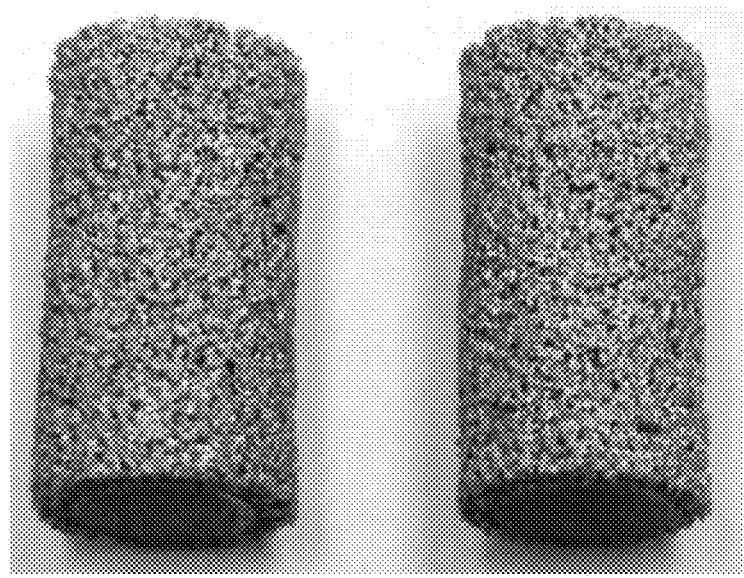
FIG. 7 is a photograph of an implant prepared according to the invention.

The implant substrates had a diameter of 5.7 and length of 10 mm. The coating thickness was 1.2 mm, with a mean pore size of 200 microns and a porosity of 63% by volume. FIG. 7 is a photograph of the coated components.

EXAMPLE VI

Figure 8:
FIG. 8 is an x-ray photograph of implants of the invention implanted into a mammalian host.

A transcortical implant model was utilized following the protocol of Bobyn et al., The optimum pore size for the fixation of porous-surfaced metal implants by the ingrowth of bone, Clin Orthop 150: 263, 1980. This involved the placement of implants into holes drilled into the lateral cortices of canine femora and subsequent analysis of the bone-implant interface using histology. The hosts for the experiments were three mature mongrel dogs weighing between 30 and 35 kg. Using a posterolateral approach to the femur, a four to five inch incision was made through the skin (from a point about 3 inches distal to the trochanter extending to about 1 inch above the femoral condyles). The fascia latae covering the thigh muscle was incised and the vastus lateralis retracted anteriorly from the intermuscular septum to expose the femur. Two holes were drilled in the lateral cortex using a 5.6 mm drill with spacing about 1.5 cm apart, as show in FIG. 8. The implants were tapped into the drill sites with a slight interference fit, leaving 2-3 mm extending out of the femur. The site was irrigated with saline and the incision was closed in standard layered fashion using Vicryl sutures.

The test protocol resulted in two data points at each of four weeks, eight weeks and 12 weeks. The harvested femora were divided with a band saw into short segments for histological processing. The implants were processed for histological examination of the bone-implant interface. This involved dehydrating in ascending solutions of ethanol, defatting in a 1:1 solution of ether-acetone, infiltration under vacuum and embedding with polymethylmethacrylate, and sectioning the implant longitudinally with a low-speed cut-off apparatus. Sections were polished and sputter coated with gold-palladium prior to imaging with backscattered scanning electron microscopy.

Figure 9:
FIGS. 9 and 10 are backscattered scanning electron micrographs of implants of the invention according to a working example.
Figure 10:
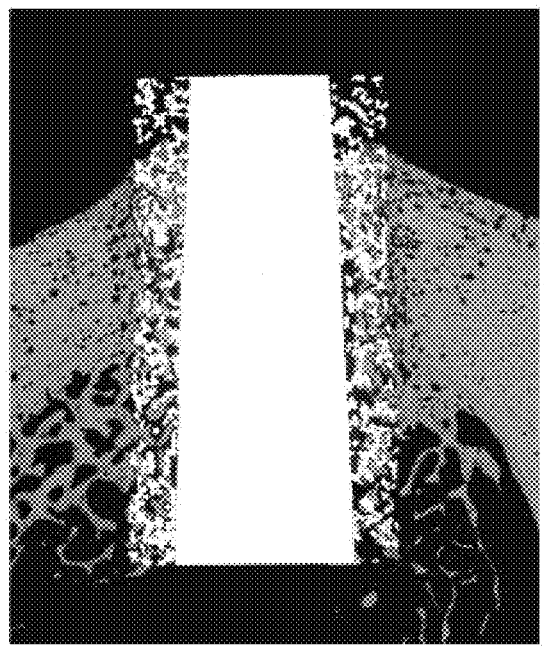

Bone growth into the Co—Cr—Mo porous structure was observed in all implants at all time periods to varying extents. At four weeks, immature new bone had developed within the outermost porous implant region adjacent to native cortical bone and to a lesser extent within the intramedullary canal. By eight weeks dense and much more uniform bone had filled most of the implant pores adjacent to the native cortex, within most of the porous coating for implants. This is evident from FIG. 9, which is a backscattered scanning electron micrograph of a longitudinal section of a porous coated dipped implant at eight weeks illustrating a mature bone ingrown interface. FIG. 10 is a backscattered scanning electron micrograph of a longitudinal section of a porous coated dipped implant at 12 weeks. The interface is more mature than at eight weeks, with very dense bone formation within most of the porous coating.

This study confirmed the inherent suitability of the porous Co—Cr—Mo biomaterial coating of the invention for biologic fixation by bone ingrowth. Compared with the historical sintered beaded Co—Cr—Mo porous implants of Bobyn et al., a very similar bone ingrowth response was observed, with calcified tissue present within most of the porous coating already by eight weeks after surgery. This is notable since the same surgical and histological protocols were followed and the sintered beaded implants have a long history of successful clinical utilization. The histological picture associated with the Co—Cr—Mo porous coating also compared very favorably with other porous materials in present clinical use.

EXAMPLE VII

Figure 11:
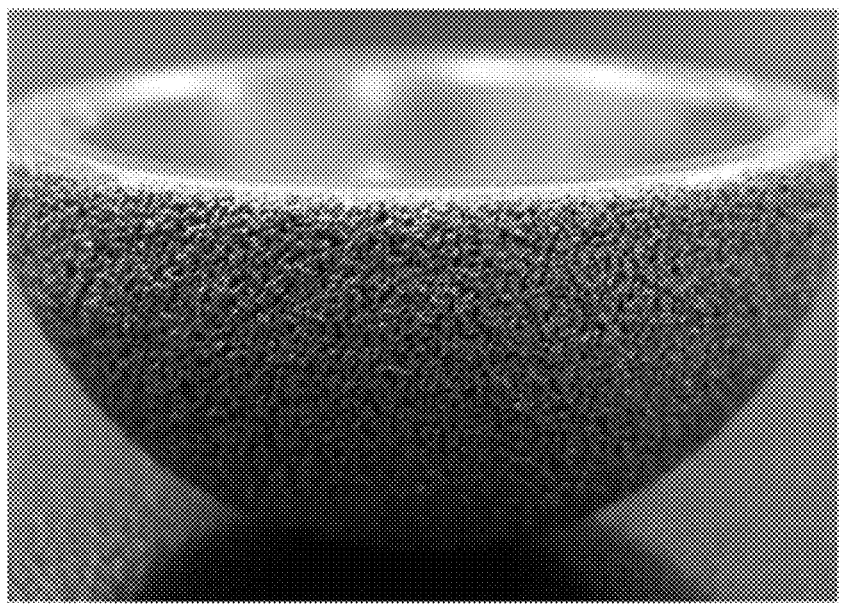
FIGS. 11 and 12 are photographs of implants of the invention.
Figure 12:

One acetabulum for hip joint and one knee replacement component were prepared by the process of the invention using the rough porous Co—Cr—Mo coating of the invention, and are shown in FIGS. 11 and 12. In most embodiments of the invention, the surgical implant has external bone ingrowth surfaces bearing the rough porous coating and other major surfaces which do not bear the rough porous coating, such as in FIGS. 11 and 12, where the coating is only on the major surface shown, and is not on the side edges or on the opposite major surfaces. When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the invention are achieved and other advantageous results attained.

The above description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

The invention claimed is:

1. A surgical implant component comprising:
    an implant component body manufactured from a Co-based substrate alloy comprising Co, Cr, Mo, Si, and C; and
    a coating on a bone-ingrowth surface of the component body manufactured from a Co-based coating alloy comprising Co, Cr, Mo, Si, C and B;
    wherein the coating is a network of fused particles of the Co-based coating alloy, the network of fused particles forming an exterior surface on the bone-ingrowth surface and including a mixture between 60 and 90 volume % spherical particles and between 10 and 40 volume % irregular aspherical particles;
    and at least about 70 volume % of the spherical particles have a particle size between about 75 and about 150 microns and at least about 70 volume % of the irregular aspherical particles have a particle size between about 355 and about 425 microns;

and wherein the coating further comprises pores and between about 35 and about 70 volume % porosity.

2. The surgical implant of claim 1 wherein:

the Co-based coating alloy has a composition which is different from a composition of the Co-based substrate alloy, and contains one of a, b, and c, as follows: a) at least 10% more C relative to C concentration of the Co-based substrate alloy, or b) at least 10% more B relative to a B concentration of the Co-based substrate alloy, or c) at least 10% more C relative to the C concentration of the Co-based substrate alloy and at least 10% more B relative to the B concentration of the Co-based substrate alloy; and wherein the Co-based coating alloy composition has a solidus temperature which is less than a solidus temperature of the Co-based substrate alloy.

3. The surgical implant of claim 2 wherein the solidus temperature of the coating alloy is at least about 5° C. lower than the solidus temperature of the substrate alloy.

4. The surgical implant of claim 1 wherein at least about 90 vol % of the pores in the coating have a pore size between about 50 and about 250 microns.

5. The surgical implant of claim 2 wherein at least about 90 vol % of the pores in the coating have a pore size between about 50 and about 250 microns.

6. The surgical implant of claim 3 wherein at least about 90 vol % of the pores in the coating have a pore size between about 50 and about 250 microns.

7. The surgical implant of claim 1 wherein at least about 90 vol % of the pores in the coating have a pore size between about 50 and 250 microns.

8. The surgical implant of claim 1 wherein:

the Co-based coating alloy has a composition which is different from a composition of the Co-based substrate alloy, and contains one of a, b, and c, as follows: a) at least 10% more C relative to C concentration of the Co-based substrate alloy, or b) at least 10% more B relative to a B concentration of the Co-based substrate alloy, or c) at least 10% more C relative to the C concentration of the Co-based substrate alloy and at least 10% more B relative to the B concentration of the Co-based substrate alloy;

the Co-based coating alloy composition has a solidus temperature which is less than a solidus temperature of the Co-based substrate alloy;

at least about 70 vol % of the spherical particles have a particle size between about 75 and about 150 microns;

at least about 70 vol % of the irregular aspherical particles have a particle size between about 355 and about 425 microns; and at least about 90 vol % of the pores in the coating have a pore size between about 50 and about 250 microns;

wherein the Co-based coating alloy composition has a solidus temperature which is at least about 5° F. less than a solidus temperature of the Co-based substrate alloy.

9. The surgical implant component of claim 1 wherein the Co-based substrate alloy comprises:

from about 27 to about 30 wt % Cr,
from about 5 to about 7 wt % Mo,
up to about 1.0 wt % Si,
C in a concentration of up to about 0.35 wt % C, incidental impurities totaling less than 4 wt % including no more than 0.75 wt % Fe and no more than 0.5 wt % Ni, and balance Co.

10. The surgical implant component of one of claim 1 wherein the Co-based substrate alloy comprises:

from about 23 to about 33 wt % Cr,
from about 8 to about 20 wt % Mo,
up to about 1.5 wt % Si,
from about 1.5 to about 3.5 wt % C, incidental impurities totaling less than 4 wt % including no more than 1 wt % Fe and no more than 1 wt % Ni, and balance Co.

11. The surgical implant component of claim 1, wherein the exterior surface has a coefficient of friction of at least 0.65.

12. The surgical implant component of claim 1, wherein the exterior surface has an average coefficient of friction of 0.4 to 0.8.

13. The surgical implant component of claim 1, wherein the mixture comprises between 65 and 75 volume percent spherical particles and between 25 and 35 volume percent irregular aspherical particles.

* * * * *